United States Patent [19]

Sakamoto et al.

[11] 4,250,339
[45] Feb. 10, 1981

[54] PROCESS FOR PRODUCING METHACROLEIN

[75] Inventors: Teruhisa Sakamoto; Kazuhiko Sekizawa; Keiichi Kihara, all of Shin-nanyo, Japan

[73] Assignee: Toyo Soda Manufacturing Co., Ltd., Shin-nanyo, Japan

[21] Appl. No.: 98,774

[22] Filed: Nov. 30, 1979

[30] Foreign Application Priority Data

Nov. 22, 1978 [JP] Japan .................................. 53-157590

[51] Int. Cl.³ ...................... C07C 45/35; C07C 45/37
[52] U.S. Cl. .................................. 568/471; 568/479; 562/534; 562/538; 562/546; 252/432
[58] Field of Search .............. 260/603 C, 604 R; 568/471, 479; 252/432; 562/438, 446

[56] References Cited

U.S. PATENT DOCUMENTS

| | | | |
|---|---|---|---|
| 4,035,418 | 7/1977 | Okada et al. | 260/604 R |
| 4,087,462 | 5/1978 | Neugebauer et al. | 260/603 C |
| 4,111,984 | 9/1978 | Ishii et al. | 260/604 R |
| 4,148,757 | 4/1979 | Brazdil et al. | 260/604 R |
| 4,155,938 | 5/1979 | Yamamoto et al. | 260/604 R |
| 4,166,808 | 9/1979 | Daumas et al. | 260/604 R |
| 4,186,152 | 1/1980 | Yamamoto et al. | 260/604 R |

OTHER PUBLICATIONS

Kawakami et al., Chem. Abst., vol. 85, #77656F (1976).
Grasselli et al., Chem. Abstr., vol. 84, #112327c (1976).
Sakakibara et al., Chem. Abstr., vol. 84, #22698v (1976).
Takenaka et al., Chem. Abstr., vol. 71, #49280w (1969).
Takayama et al., Chem. Abstr., vol. 74, #80304t (1971).

*Primary Examiner*—James H. Reamer
*Attorney, Agent, or Firm*—Olbon, Fisher, Spivak, McClelland & Maier

[57] ABSTRACT

Methacrolein is produced by a vapor phase oxidation of isobutylene or tertiary butanol in the presence of a complex oxide catalyst having the formula $$Mo_aCo_bFe_cBi_dTl_eX_fY_gZ_hO_i$$

wherein X represents V and/or Nb; Y represents La and/or Ce; and Z represents Cs and/or Te and a, b, c, d, e, f, g, h and i represent atomic ratios wherein a=12; b=3 to 15; c=0.4 to 5; d=0.4 to 5; e=0.01 to 2; f=0.01 to 2; g=0 to 2; h=0 to 2; and i is determined by the valences of the non-oxygen components of the catalyst and is usually in a range of 40 to 79.

6 Claims, No Drawings

PROCESS FOR PRODUCING METHACROLEIN

BACKGROUND OF THE INVENTION

1. Field of the Invention

The present invention relates to a process for producing methacrolein by a vapor phase catalytic oxidation of isobutylene or tertiary butanol. More particularly, it relates to a process for producing methacrolein by a vapor phase catalytic oxidation of isobutylene or tertiary butanol in the presence of a novel complex oxide catalyst comprising components of Mo, Co, Fe, Bi, Tl, V and/or Nb, if necessary, La and/or Ce, Cs and/or Te.

2. Description of the Prior Arts

The processes for producing unsaturated aldehydes such as acrolein or methacrolein by vapor phase catalytic oxidations of lower α-olefins such as propylene or isobutylene, have been proposed in many patent applications. In most of the cases, complex oxide catalysts comprising components of Mo, Co and/or Ni, Fe and Bi and other elements have been used. Various additional elements have been proposed as described in Japanese Unexamined Patent Publication No. 34107/1976, and No. 40,391/1976, etc.

In order to increase selectivity of the object compound of the unsaturated aldehyde, it has been known that the incorporation of thallium is effective for the oxidation of isobutylene. Furthermore, it has been proposed to incorporate an alkali metal component such as K, Rb and Cs, or the other component of P, As, B or Sb.

The incorporation of these component may improve the selectivity, but may decrease the activity. In some cases, the decrease of the activity is caused during the reaction. Thus, these processes have not been always satisfactory. In view of industrial operations, it is important to give high selectivity in high conversion, that is, high catalytic function for high per-pass yield. The inventors have studied on the improvement of the catalysts.

SUMMARY OF THE INVENTION

It is an object of the present invention to provide a process for producing methacrolein by a vapor phase catalytic oxidation of isobutylene or tertiary butanol in high selectivity and high conversion, that is, high per-pass yield.

It is another object of the present invention to provide remarkably high per-pass yield of methacrolein by incorporating components of Tl, V and/or Nb into a Mo-Co-Fe-Bi type complex oxide catalyst.

The other object of the present invention is to provide further improved result by incorporating components of La and/or Ce and Cs and/or Te.

The foregoing and other objects of the present invention have been attained by producing methacrolein by a vapor phase catalytic oxidation of isobutylene or tertiary butanol in the presence of a complex oxide catalyst having the formula:

$$Mo_a Co_b Fe_c Bi_d Tl_e X_f Y_g Z_h O_i$$

wherein X represents V and/or Nb; Y represents La and/or Ce; and Z represents Cs and/or Te and a, b, c, d, e, f, g, h, and i represent atomic ratios wherein a=12; b=3 to 15; c=0.4 to 5; d=0.4 to 5; e=0.01 to 2; f=0.01 to 2; g=0 to 2; h=0 to 2 and i is determined by the valences of the non-oxygen components of the catalyst and is usually in a range of 40 to 79.

DETAILED DESCRIPTION OF THE PREFERRED EMBODIMENTS

The catalyst of the present invention is effective when the components are present in the above-mentioned quantities. An epecially excellent activity can be obtained by using a complex oxide catalyst having the formula $$Mo_{a'} Co_{b'} Fe_{c'} Bi_{d'} Tl_{e'} X_{f'} Y_{g'} Z_{h'} O_{i'}$$

wherein a′=12; b′=4 to 12; c′=0.5 to 3; d′=0.5 to 3; e′=0.05 to 1; f′=0.05 to 1; g′=0.05 to 1; h′=0.05 to 1; and i′ is determined by the valences of the non-oxygen components of the catalyst and usually 42 to 64.

The catalyst of the present invention can be prepared by the known desired methods, and is usually prepared by a precipitation-concentrating method or an impregnation-supporting method or the like. The starting materials for the elements of the catalysts of the present invention are preferably water soluble compounds such as ammonium salts, nitrates or chlorides. Suitable sources of molybdenum include para-ammonium molybdate, molybdic acid and the like. Suitable sources of vanadium include ammonium metavanadate, vanadium pentoxide, vanadium oxydichloride, vanadium trichloride, vanadium trioxide and the like. Suitable sources of cobalts include cobalt nitrate and the like. Suitable sources of iron include ferric nitrate, ferrous chloride, ferric chloride and the like. Suitable sources of bismuth include bismuth nitrate and the like. Suitable sources of thallium include thallium nitrate and the like.

In a typical method of preparation of the catalyst, an aqueous solution of cobalt nitrate, ferric nitrate and thallium nitrate is added to an aqueous solution of ammonium molybdenate and ammonium metavanadate and then, an aqueous solution of nitric acid containing bismuth nitrate was added and then, an aqueous solution of cerium nitrate and cesium nitrate or niobium pentoxide and tellium dioxide are added to the mixture.

The complex oxide catalyst of the invention can be prepared by adding a silica component as a carrier such as diatomaceous earth, kaolin, silica sol, silicone carbide, silica-alumina and the like at a ratio of about 2 to 20 wt.% as $SiO_2$. The mixture is concentrated with stirring and dried and molded and calcined at 450° to 600° C. in air to obtain the catalyst.

The starting material used for the process of the present invention is isobutylene or tertiary butanol. Isobutylene can be isobutylene-containing hydrocarbons as spent B-B fraction obtained by a butadiene extraction. The molecular oxygen can be pure oxygen, an oxygen enriched air and air. It is preferably air.

The feed gas preferably contains 0.5 to 10 vol.% of isobutylene or tertiary butanol; 5 to 20 vol.% of molecular oxygen; 0 to 60 vol.% of steam and 20 to 80 vol.% of nitrogen. It is possible to use an inert gas such as carbon dioxide or argon as a diluent.

The reaction temperature is preferably in a range of 250° to 450° C. and the reaction pressure is preferably in a range of atmospheric pressure to 10 atm. and the contact time is preferably in a range of 0.5 to 10 seconds. The process of the present invention can be carried out in a fixed bed system as well as in a fluidized bed system.

The present invention will be further illustrated by certain examples and references which are provided for purposes of illustration only.

The characteristics of the present invention is to give high selectivity in high conversion and to give high per-pass yield of methacrolein and methacrylic acid such as higher than 85% and also to give high catalytic activity.

EXAMPLE 1

In 600 ml of a distilled water heated at about 80° C. was dissolved 212 g of ammonium paramolybdenate. The solution was heated and stirred and 400 ml of an aqueous solution containing 232.8 g of cobalt nitrate, 80.8 g of ferric nitrate and 13.3 g of thallium nitrate was added. The mixture was admixed with 200 ml of an aqueous solution of dilute nitric acid containing 72.8 g of bismuth nitrate and then, further admixed with 100 ml of an aqueous solution of dilute hydrochloric acid containing 7.9 g of vanadium trichloride. They were further stirred and then, 37.0 g of diatomaceous earth was added. The mixture was heated with stirring to concentrate it. The resulting slurry was concentrated and dried and then, the dried product was molded and calcined at 500° C. for 5 hours in air.

The catalyst obtained has the formula as atomic ratios:

$Mo_{12}Co_8Fe_2Bi_{1.5}Tl_{0.5}V_{0.5}O_{51}$ (10 wt.% of $SiO_2$).

The mixed gas containing 5.0 vol.% of isobutylene, 35 vol.% of steam and 60 vol.% of air was fed into a catalyst layer at 370° C. for a contact time of 2.0 seconds (based on 1 atm. at 0° C.) to react them. As a result, the conversion of isobutylene was 97.3%, the selectivity to methacrolein was 80.1%, the selectivity to methacrylic acid was 3.7% and the per-pass yield of methacrolein and methacrylic acid was 81.5%.

EXAMPLE 2

The process of Example 1 was followed except that 13.5 g of niobium pentachloride was used instead of 7.9 g of vanadium trichloride to obtain a catalyst. The catalyst has the formula as atomic ratios:

$Mo_{12}Co_8Fe_2Bi_{1.5}Tl_{0.5}Nb_{0.5}O_{51}$ (10 wt.% of $SiO_2$).

The reaction was carried out in the condition of Example 1 by using the catalyst. As a result, the conversion of isobutylene was 96.8%, the selectivity to methacrolein was 80.4%, the selectivity to methacrylic acid was 3.5% and the per-pass yield of methacrolein and methacrylic acid was 81.2%.

EXAMPLE 3

The catalyst obtained in Example 1 was used to react tertiary butanol.

A mixed gas containing 5.0 vol.% of tertiary butanol, 35 vol.% of steam and 60 vol.% of air was fed into a catalyst layer at 380° C. for a contact time of 2.0 seconds (based on 1 atm. at 0° C.) to react them. As a result, the conversion of tertiary butanol was 98.4%, the selectivity to methacrolein was 80.5%, the selectivity to methacrylic acid was 2.8% and the per-pass yield of methacrolein and methacrylic acid was 82.0%.

EXAMPLE 4

The process of Example 3 was followed except that the catalyst obtained in Example 2 was used. As a result, the conversion of tertiary butanol was 98.0%, the selectivity to methacrolein was 79.6%, the selectivity to methacrylic acid was 3.2% and the per-pass yield of methacrolein and methacrylic acid was 81.1%.

EXAMPLE 5

In 600 ml of a distilled water heated at about 80° C. were dissolved 212 g of ammonium paramolybdenate and 5.9 g of ammonium metavanadate. 400 Ml of an aqueous solution containing 232.8 g of cobalt nitrate, 80.8 g of ferric nitrate and 13.3 g of thallium nitrate was added dropwise to the solution with stirring and then, the mixture was admixed with 200 ml of an aqueous solution of nitric acid containing 72.8 g of bismuth nitrate and 8.7 g of cerium nitrate and then, 37.0 g of diatomaceous earth was added. The mixture was heated with stirring to concentrate it. The resulting slurry was concentrated and dried and then, the dried product was moled and calcined at 500° C. for 5 hours in air.

The catalyst obtained has the formula as atomic ratios:

$Mo_{12}Co_8Fe_2Bi_{1.5}Tl_{0.5}V_{0.5}Ce_{0.2}O_{52}$ (10 wt.% of $SiO_2$).

The reaction was carried out in the condition of Example 1 by using the catalyst. As a result, the conversion of isobutylene was 98.6%, the selectivity to methacrolein was 79.7%, the selectivity to methacrylic acid was 4.2%, and the per-pass yield of methacrolein and methacrylic acid was 82.7%.

REFERENCE 1

The process of Example 5 was followed except that the vanadium component and the cerium component were not added to obtain a catalyst. The catalyst has the formula as atomic ratios:

$Mo_{12}Co_8Fe_2Bi_{1.5}Tl_{0.5}O_{50}$ (10 wt.% of $SiO_2$).

The reaction was carried out in the condition of Example 1 by using the catalyst. As a result, the conversion of isobutylene was 91.3%, the selectivity to methacrolein was 78.4%, the selectivity to methacrylic acid was 3.5% and the per-pass yield of methacrolein and methacrylic acid was 74.8%.

EXAMPLE 6

In 400 ml of a distilled water heated at about 80° C. was dissolved 212 g of ammonium paramolybdenate. 400 Ml of an aqueous solution containing 232.8 g of cobalt nitrate, 80.8 g of ferric nitrate and 13.3 g of thallium nitrate was added to the solution with stirring and then, the mixture was admixed with 200 ml of an aqueous solution of diluted nitric acid containing 72.8 g of bismuth nitrate and 3.9 g of cesium nitrate and further 6.6 g of niobium pentoxide and 37.2 g of diatomaceous earth was added. The mixture was heated with stirring to concentrate it. The resulting slurry was concentrated and dried and then, the dried product was molded and calcined at 500° C. for 5 hours in air.

The catalyst obtained has the formula as atomic ratios:

$Mo_{12}Co_8Fe_2Bi_{1.5}Tl_{0.5}Nb_{0.5}Cs_{0.2}O_{51}$ (10 wt.% of $SiO_2$).

The reaction was carried out in the condition of Example 1 by using the catalyst. As a result, the conversion of isobutylene was 95.7%, the selectivity to methacrolein was 84.3%, the selectivity to methacrylic acid was 3.4% and the per-pass yield of methacrolein and methacrylic acid was 83.9%.

REFERENCE 2

The process of Example 6 was followed except that the thallium component and the niobium component were not added to obtain a catalyst. The catalyst had the formula as atomic ratios:

$Mo_{12}Co_8Fe_2Bi_{1.5}Cs_{0.2}O_{50}$ (10 wt.% of $SiO_2$).

The reaction was carried out in the condition of Example 1 by using the catalyst. As a result, the conversion of isobutylene was 99.3%, the selectivity to methacrolein was 64.7%, the selectivity to methacrylic acid was 4.1%, and the per-pass yield of methacrolein and methacrylic acid was 68.3%.

EXAMPLE 7

The process of Example 5 was follows except that 21.7 g of lanthanum nitrate and 3.2 g of tellurium dioxide instead of 8.7 g of cerium nitrate, to obtain a catalyst. The catalyst had the formula as atomic ratios:

$Mo_{12}Co_8Fe_2Bi_{1.5}Tl_{0.6}V_{0.5}La_{0.5}Te_{0.2}O_{53}$ (10% of $SiO_2$).

The reaction was carried out in the condition of Example 1 by using the catalyst. As a result, the conversion of isobutylene was 98.0%, the selectivity to methacrolein was 82.3%, the selectivity to methacrylic acid was 3.5%, and the per-pass yield of methacrolein and methacrylic acid was 84.1.

EXAMPLE 8

In 600 ml of a distilled water heated at about 80° C., were added 212 g of ammonium paramolybdenate and 4.7 g of ammonium metavanadate. The solution was admixed with 100 ml of an aqueous solution of hydrochloric acid containing 5.4 g of niobium pentachloride while stirred. The mixture was admixed with 400 ml of an aqueous solution containing 203.7 g of cobalt nitrate, 60.6 g of ferric nitrate and 13.3 g of thallium nitrate and then 200 ml of an aqueous solution of nitric acid containing 72.8 g of bismuth nitrate, 3.9 g of cesium nitrate was added dropwise with stirring and then, 35.4 g of diatomaceous earth was added. The mixture was heated with stirring to concentrate it. The resulting slurry was concentrated and dried and then, the dried product was molded and calcined at 500° C. for 5 hours in air.

The catalyst obtained has the formula as atomic ratios:

$Mo_{12}Co_7Fe_{1.5}Bi_{1.5}Tl_{0.5}V_{0.4}Nb_{0.2}Cs_{0.2}O_{50}$ (10 wt.% of $SiO_2$).

The reaction was carried out in the condition of Example 1 by using the catalyst.

As a result, the conversion of isobutylene was 97.2%, the selectivity to methacrolein was 84.7%, the selectivity to methacrylic acid was 3.1% and the per-pass yield of methacrolein and methacrylic acid was 85.3%.

EXAMPLE 9

The process of Example 8 was followed except that 13.0 g of cerium nitrate and 6.4 g of tellurium dioxide were added instead of 3.9 g of cesium nitrate to obtain a catalyst.

The catalyst obtained has the formula as atomic ratios:

$Mo_{12}Co_7Fe_{1.5}Bi_{1.5}Tl_{0.5}V_{0.4}Nb_{0.2}Ce_{0.3}Te_{0.4}O_{51}$ (10 wt.% of $SiO_2$).

The reaction was carried out in the condition of Example 1 by using the catalyst. As a result, the conversion of isobutylene was 98.2%, the selectivity to methacrolein was 80.7%, the selectivity to methacrylic acid was 3.8% and the per-pass yield of methacrolein and methacrylic acid was 83.0%.

EXAMPLE 10

The catalyst obtained in Example 5 and $C_4$-hydrocarbons containing 43.2 vol.% of isobutylene, 26.1 vol.% of 1-butene, 10.5 vol.% of trans-2-butene, 6.4 vol.% of cis-2-butene, 10.2 vol.% of n-butane, 1.9 vol.% of isobutane and 1.7 vol.% of the other components as starting materials were used.

A mixed gas containing 8 vol.% of the isobutylene-containing $C_4$ hydrocarbons, 30 vol.% of steam and 62 vol.% of air was fed into a catalyst layer at 380° C. for a contact time of 2.0 seconds (based on 1 atm. at 0° C.) to react them. As a result, the conversion of isobutylene was 97.9%, the selectivity to methacrolein was 80.2%, the selectivity to methacrylic acid was 4.5% and the per-pass yield of methacrolein and methacrylic acid was 82.9%.

EXAMPLE 11

The process of Example 10 was followed except that the catalyst obtained in Example 8 was used. As a result, the conversion of isobutylene was 97.5%, the selectivity to methacrolein was 83.5%, the selectivity to methacrylic acid was 3.7%, and the per-pass yield of methacrolein and methacrylic acid was 85.0%.

EXAMPLE 12

The catalyst obtained in Example 5 was used to react tertiary butanol.

A mixed gas containing 5.0 vol.% of tertiary butanol, 35 vol.% of steam and 60 vol.% of air was fed into a catalyst layer at 360° C. for a contact time of 2.4 seconds (based on 1 atm. at 0° C.) to react them. As a result, the conversion of tertiary butanol was 99.0%, the selectivity to methacrolein was 80.6%, the selectivity to methacrylic acid was 3.1% and the per-pass yield cf methacrolein and methacrylic acid was 82.9%.

EXAMPLE 13

The process of Example 12 was follows except that the catalyst of Example 8 was used. As a result, the conversion of isobutylene was 97.6%, the selectivity of methacrolein was 84.8%, the selectivity to methacrylic acid was 2.9%, and the per-pass yield of methacrolein and methacrylic acid was 85.6%.

REFERENCE 3

The process of Example 12 was followed except that the catalyst obtained in Reference 2 was used. As a result, the conversion of tertiary butanol was 100%, the selectivity to methacrolein was 62.5%, the selectivity to methacrylic acid was 4.2% and the per-pass yield of methacrolein and methacrylic acid was 66.7%.

We claim:

1. A process for producing methacrolein by a vapor phase catalytic oxidation of isobutylene or tertiary butanol which comprises reacting isobutylene or tertiary butanol with molecular oxygen or a molecular oxygen-containing gas in the vapor phase at 250° to 450° C. in the presence of a complex oxide catalyst having the formula $$Mo_a Co_b Fe_c Bi_d Tl_e X_f Y_g Z_h O_i$$

wherein X represents V and/or Nb; Y represents La and/or Ce; and Z represents Cs and/or Te and a, b, c, d, e, f, g, h and i represent atomic ratios wherein a=12; b=3 to 15; c=0.4 to 5; d=0.4 to 5; e=0.01 to 2; f=0.01 to 2; g=0 to 2; h=0 to 2; and i is determined by the valences of the non-oxygen components of the catalyst and is in a range of 40 to 79.

2. A process according to claim 1 wherein the catalyst is the complex oxide catalyst having the formula $$Mo_{a'} Co_{b'} Fe_{c'} Bi_{d'} Tl_{e'} X_{f'} Y_{g'} Z_{h'} O_{i'}$$

wherein a'=12; b'=4 to 12; c'=0.5 to 3; d'=0.5 to 3; e'=0.05 to 1; f'=0.05 to 1; g'=0.05 to 1; h'=0.05 to 1 and i' is determined by the valences of the non-oxygen components of the catalyst and is in a range of 42 to 64.

3. A process according to claim 1 wherein the catalyst is supported on a carrier.

4. A process according to claim 1 wherein the catalyst is calcined at a temperature in a range of 450° to 600° C.

5. A process according to claim 1 wherein said reaction is carried out in an apparent contact time of 0.5 to 10 seconds.

6. A process according to claim 1 wherein said reaction is carried out under pressure of from atmospheric pressure to 10 atm.

* * * * *

UNITED STATES PATENT AND TRADEMARK OFFICE
CERTIFICATE OF CORRECTION

PATENT NO. : 4,250,339
DATED : February 10, 1981
INVENTOR(S) : TERUHISA SAKAMOTO ET AL It is certified that error appears in the above—identified patent and that said Letters Patent is hereby corrected as shown below:

Please correct the Foreign Application Priority Data to read as follows:

[30]--Foreign Application Priority Data

Dec. 22, 1978 [JP]  Japan......53-157590  --rather than--

[30]--Foreign Application Priority Data

Nov. 22, 1978 [JP]  Japan......53-157590 as it now appears.

Signed and Sealed this

Twenty-eighth Day of April 1981

[SEAL]

Attest:

RENE D. TEGTMEYER

Attesting Officer

Acting Commissioner of Patents and Trademarks